United States Patent [19]

Reinbold et al.

[11] 4,372,979

[45] Feb. 8, 1983

[54] REDUCTION OF CURD FINES IN CHEESE MANUFACTURE

[75] Inventors: George W. Reinbold, Wheat Ridge; Malireddy S. Reddy, Thornton, both of Colo.

[73] Assignee: Leprino Foods Company, Denver, Colo.

[21] Appl. No.: 236,717

[22] Filed: Feb. 23, 1981

Related U.S. Application Data

[63] Continuation-in-part of Ser. No. 73,330, Sep. 7, 1979, abandoned.

[51] Int. Cl.$^3$ .................... A23C 19/02; A23C 21/02; C12N 1/20
[52] U.S. Cl. ........................................ 426/36; 426/41; 426/43; 435/253
[58] Field of Search ...................... 426/41, 43, 42, 34; 435/253

[56] References Cited

U.S. PATENT DOCUMENTS

| | | | |
|---|---|---|---|
| 3,354,049 | 11/1967 | Christensen | 435/253 |
| 3,852,158 | 12/1974 | Anderson et al. | 426/43 X |
| 3,998,700 | 12/1976 | Reinbold et al. | 426/41 |
| 4,053,642 | 10/1977 | Hup et al. | 426/43 X |
| 4,110,476 | 8/1978 | Rhodes | 426/43 X |
| 4,115,199 | 9/1978 | Porubcan et al. | 426/43 X |

OTHER PUBLICATIONS

Hall et al., Drying of Milk and Milk Products, 2nd Ed., The Avi Publishing Co., Inc., Westport, Conn., 1971, (p. 172).

Primary Examiner—David M. Naff

[57] ABSTRACT

Bulk starter cultures for use in cheese manufacture are prepared from a whey solids-containing culture medium. The medium is rennet-coagulable but remains uncoagulated throughout fermentation to produce the bulk starter culture. As used in cheese making, the medium is characterized by being substantially free of curd fines, and by the protein of the medium coagulating with the milk in the cheese vat, thereby increasing cheese yield.

18 Claims, No Drawings

REDUCTION OF CURD FINES IN CHEESE MANUFACTURE

REFERENCE

This application is a continuation-in-part of copending application Ser. No. 73,330, filed Sept. 7, 1979, and now abandoned.

BACKGROUND AND PRIOR ART

Whey protein solids, such as spray-dried sweet whey or acid whey, delactosed whey, and whey protein concentrate, have been used to provide part or all of the protein and lactose solids in media for preparing bulk starter cultures in the manufacture of cheese. After preparation, the media are inoculated with the lactic acid-producing bacteria desired for manufacturing the particular cheese, and the bacteria are cultured therein to produce the starter culture for addition to the milk in the cheese vat. The whey protein does not coagulate in the cheese vat with the casein, but part of the protein of the starter media will be in a denatured or precipitated form, which can become associated with the coagulated casein by physical entrapment. By the mixing and stirring of the curd in the cheese vat, most of the precipitated protein of the starter culture, as well as the small fragments of curd released during cutting and stirring (referred to as "curd dust" or "fines") can be removed from the curd and will pass out of the vat with the whey. When the whey is passed through a screen, as is conventional practice, the curd dust or fines accumulate on the screen, but complete removal of the smaller sized fines is not obtained. An additional pre-filtration step is therefore required when the whey is to be subjected to ultrafiltration.

It would therefore be desirable to provide a method for preparing substantially fine-free starter media from whey solids, and especially if the whey protein will coagulate with the casein in the cheese vat forming a true total coagulum. The quantity of cheese produced would thereby be increased, there would be no entrapment of precipitated protein which was not in the proper coagulated form, and there would be greater reduction of fines amount as well as an improvement in the quality of the fines, i.e., the fines would more nearly resemble true cheese curd. Heretofore, however, the art has failed to provide such a method.

In preparing bulk starter cultures, whey solids have been combined with milk solids. See U.S. Pat. Nos. 3,852,158, 4,020,185 and 3,998,700. Yogurt has also been prepared by using mixtures of whey protein and milk solids, as described in U.S. Pat. No. 4,110,476. The latter patent discloses that the whey proteins are utilized to protect the casein of the milk protein against coagulation during the manufacture of the liquid yogurt.

Interactions of casein with serum protein have been described in the literature. See Fundamentals of Dairy Chemistry (2nd Ed., 1974), Chapt. 11, 628-631. Whey protein is comprised of serum protein, namely, the lactalbumins and lactoglobulins. Commercial applications of the interaction or "complexing" of casein and serum protein or whey protein have been proposed. See French Pat. No. 1,528,103; Polish Pat. No. 82,699; and Schw. Milch. Forsch., 4, 1-8 (1975). As described in the cited French patent, a calcium salt is added to milk, which is then heated to a temperature at which the complex of casein and serum protein precipitates. The Polish patent proposes the addition of a calcium salt to milk, which is then pasteurized to complex the casein and whey protein, and then used to prepare cheese in the usual way by the addition of a starter culture and rennet. The last-cited reference proposes the addition of whey, such as a whey protein concentrate, to milk. After addition of calcium chloride the milk-whey mixture is heated to complex the casein and whey protein, which is then coagulated, corresponding to rennet coagulation in the manufacture of cheese.

SUMMARY OF INVENTION

The method of the present invention provides a means for preparing from whey solids a substantially fine-free rennet-coagulable bulk culture for use in manufacturing cheese. The aqueous culture media contain a substantial proportion of whey solids which are preferably provided by whey protein concentrate. The whey protein-providing whey solids are used in combination with milk solids, or precipitated casein in a water-dispersible form such as calcium caseinate. In a presently preferred embodiment, whey protein concentrate is used in admixture with calcium caseinate. In accordance with the present invention, the ratio of casein to serum protein is selected to provide sufficient casein for complexing the heat-coagulable whey protein. The medium is heated under conditions of pH, temperature, and time which promote the complexing of the casein and serum protein without precipitating the serum protein or coagulating the medium. On completion of the heating, the medium is rennet-coagulable. After inoculation with the desired lactic acid-producing bacteria, the bacteria are cultured therein to produce the bulk starter culture. The culturing is controlled with respect to temperature and pH so that coagulation of the medium is avoided. On completion of the fermentation, however, the medium remains subject to rennet-coagulation and is substantially free of precipitated serum protein. Therefore, on addition to the cheese vat, the protein of the medium (complexed casein and whey protein) coagulates at the same time as the casein of the milk, and produces a curd-whey mixture which is substantially free from culture medium produced curd dust or fines.

DESCRIPTION OF PREFERRED EMBODIMENTS

The present invention may be practiced with whey solids containing soluble whey protein. Whey solids obtained by spray-drying sweet whey or acid whey contain about 12-13% whey protein (serum protein). Higher concentrations of whey protein can be obtained by removing part of the lactose from the whey, and such delactosed whey solids (16 to 27% protein) can be used in the present invention. A preferred source of whey solids is whey protein concentrate (WPC) which is obtained by ultrafiltration of sweet whey or acid whey. Typically, such WPC will comprise 28-33% whey protein. WPC containing up to 50% protein can be advantageously used. The ultrafiltrate or retentate produced by the ultrafiltration is usually condensed in an evaporator and further treated in a spray dryer to produce the dry product containing 28% or more of whey protein. In general, the concentrated whey should contain at least 16% and preferably 20% or more whey protein. (All percentages are by weight.)

The concentrated whey solids, which provide the whey protein, are used in combination with media solids providing casein or a casein salt, such as calcium caseinate, for complexing with the whey protein. For example, good results are obtained with calcium caseinate. Where calcium caseinate is not commercially available, precipitated casein may be resolubilized, so that it is in a water-dispersible salt form, such as the calcium, sodium, or magnesium salt. Precipitated casein which is in a water-dispersible form, such as calcium caseinate, may be distinguished from the natural casein of milk, which may be referred to as native or unprecipitated casein.

In general, aqueous culture media for use in practicing the present invention may contain from 6 to 21% by weight of the media solids which provide the protein. A preferred concentration range is from 12 to 18% solids in the media. As used herein the term "whey solids" refers to the solids of whey as separated from cheese curd or milk in making cheese, buttermilk, etc. The term "whey protein" refers to the serum protein of whey, and not to the serum protein of milk or milk solids which has not been processed to cause separation of the whey. In certain media coming within the scope of the present invention, the total serum protein will comprise serum protein from milk solids as well as serum protein from whey solids.

The mixtures of protein-providing solids which may be used in practicing the present invention include (i) mixtures of whey solids and precipitated casein in water-dispersible form, or (ii) mixtures of whey solids in milk solids, or (iii) mixtures of whey solids, milk solids, and precipitated casein in water-dispersible form. In general, the media solids should provide a weight ratio within the range from 0.4 to 5.0 parts of casein per part of total serum protein. The proportion is calculated on a casein basis even if the casein is provided in salt form, such as calcium caseinate. The advantages of the present invention appear to be maximized in the range from 0.9 to 3.5 parts of casein (casein basis) per part of total serum protein. For example, from 1 to 3 parts of casein or calcium caseinate (casein basis) can advantageously be used per part of serum protein, which is preferably the whey protein concentrate (WPC). Whatever the source of the whey protein, the whey protein should comprise a substantial portion of the protein of the media solids. In general, the whey protein of the whey solids comprise at least 10% by weight of the media solids. When this amount is provided by WPC, the whey protein solids will usually comprise at least 30% of the total solids, and this level is preferred with reference to the amount of whey protein solids to be used.

As indicated, the whey protein should be in substantially soluble form. If it has been denatured, such as by heating, to an extent that it is no longer soluble and cannot be resolubilized, then it is not useable in the present invention. Further, as already indicated, the casein should be either in its natural water-dispersible form of milk or milk solids, such as non-fat dry milk solids, or if precipitated as casein, it should be converted to a water-dispersible salt form.

In accordance with known practice, other minor ingredients may be incorporated in the medium, such as stimulants to promote the growth of the bacteria, or phage inhibitors, such as phosphates. (See United States Patent 3,041,248.) The present invention is concerned primarily with the protein content of the media solids.

To complete the preparation of the medium, the solids are dispersed and/or dissolved in the water to the desired concentration, such as a concentration of 9 to 12% solids by weight. The culture medium will usually not require pH adjustment and will be at a suitable pH. In general, for carrying out the heating step of the present invention, the pH may range from about 5.6 to 6.9. Conventional pH's for starter cultures may therefore be used. The media is preferably stirred continuously to maintain a uniform distribution of the solids, and while stirring is continued, it is heated to a temperature and for a time promoting the complexing of the casein and serum protein without precipitating serum protein or coagulating the medium. For example, the medium may be heated to a temperature in the range of 160° to 195° F. for 20 to 90 minutes. Good results are obtained with a heating period of 1 hour using a temperature of 185°-190° F. Under these conditions, and when the medium contains the proper ratio of casein to total serum protein (milk serum protein and whey serum protein), the complexing of the casein and serum protein is obtained without precipitation of serum protein and heat coagulation is avoided. On completion of the heating step, the suitability of the media for use in practicing the present invention can be checked by determining its rennet-coagulability. This test may be carried out with the medium at pH 6.2 and 92° F. by adding rennet at the rate of 3 ounces per one thousand pounds of medium. When the medium coagulates and forms the type of gel associated with rennet-coagulation of milk casein, the medium is suitable for use.

Under some conditions, the medium may contain ions which affect rennet-coagulability. For example, if a calcium salt or a phosphate salt has been added, the calcium ions or the phosphate ions will have an effect. The presence of added calcium ions tends to promote rennet-coagulability and a very firm coagulum may result. In the presence of added phosphate ions, calcium ions are complexed and therefore unavailable at the pH of the medium as prepared. This procedure for making the medium phage resistant will also interfere with rennet-coagulation. However, as the pH of the medium drops during the bacterial fermentation, the calcium is liberated, and the medium can be coagulated by rennet without added calcium. Therefore, when the process is applied to a phage-resistant medium, tests for rennet coagulability should be performed on a corresponding medium without the added phosphate.

The prepared medium is then employed as a culture medium for the lactic acid-producing bacteria desired for producing the particular kind of cheese. The culturing is carried out in the usual way, using a temperature favorable to the growth of the particular bacterial species. For example, culture temperatures of from about 60° to 110° F. may be used. One important difference is that the pH of the medium is not allowed to drop to a pH at which the medium coagulates. For example, the fermentation would usually be permitted to continue until the pH dropped below 5.0, such as a pH of 4.8 at which the medium coagulates. Since the complex of the casein and serum protein used in the present invention has a somewhat lower isoelectric point than that of uncomplexed casein and serum protein, a final culturing pH as low as 5.0 to 5.2 can be used without causing the medium to coagulate. If necessary, however, a reagent such as ammonium hydroxide can be added to the medium to maintain the pH at a pH above the point at which it coagulates. Usually, however, this will not be necessary, since final pH's in the range of 5.0 to 5.2 are quite satisfactory for most starter cultures when ample bacterial growth has occurred.

Any harmless lactic acid-producing cheese bacteria can be grown in the prepared medium. Where desired, mixed cultures of bacteria can be used. For manufacturing Mozzarella cheese, a mixed culture of "coccus" and "rod" bacteria can be used, such as a 3:1 to 5:1 ratio mixture of coccus to rod cells. The preferred coccus bacteria is *Streptococcus thermophilus*. The rod bacteria may be one or more lactobacilli, such as *L. bulgaricus, L. helveticus,* and *L. lactis*. Other lactic acid-producing or flavor bacteria which can be grown in the medium and the product for which they are usually used include: Swiss, Italian, and Hard Grating varieties—*S. thermophilus* and *lactobacilli* as noted. Cheddar, Stirred and Washed Curd, Colby, Brick, Muenster, Monterey Jack, Limburger, Blue, and Gorgonzola—*S. lactis* and *S. cremoris*. Cottage, Cream, and Neufchatel—*S. lactis, S. cremoris, S. diacetilactis,* and/or Leuconostoc. Cultured Buttermilk—as noted for Cottage cheese. The inoculation level is not critical and follows conventional practice. For example, the prepared medium may be inoculated with from 0.01 to 5.0% by weight of the bacterial culture. Inoculation rate, of course, depends upon growth rate of organisms used, temperature selected, and preparation of inocula (for example: liquid, frozen, concentrated, etc.). During culturing, the medium is stirred and heated in a conventional manner to promote the growth of the bacteria.

The method of the present invention is further illustrated by the following examples.

EXAMPLE I

A starter medium is prepared from nonfat dry milk, calcium caseinate, and whey protein concentrate. The nonfat dry milk and calcium caseinate may be added separately, or may be purchased as a spray-dried mixture. The composition of the medium and its preparation are set out below.

| Composition: | |
|---|---|
| Nonfat dry milk | 75 lbs. |
| Calcium caseinate | 32 lbs. |
| Whey protein concentrate (28–33% protein) | 45 lbs. |
| Water | 1198 lbs. |
| | 1350 lbs. |

Preparation

1. Clean and sanitize the starter tank thoroughly using an approved sanitizer.
2. Fill the tank with about ⅔ of the water (viz. 800 lbs.) of suitable tap water (free from inhibitory compounds).
3. Warm the water up to 110° F. and add the ingredients (according to the above formula) with the aid of a powder funnel.
4. Agitate the ingredients thoroughly until they are in complete solution, and then add rest of the water to make it up to the weight of 1350 lbs. or the equivalent of 150 gal.
5. Collect a sample of starter after adding all the ingredients. This sample can be used to determine casein, whey protein, and total protein content prior to the complexing heat treatment.
6. Heat the starter medium to 190° F. and hold for 1 hour. There should be no protein precipitation or coagulation.
7. Cool the medium to 101° to 105° F. The medium is now ready for bacterial inoculation.
8. Drain a sterile sample at this stage for determination of the casein, whey protein, and total protein content following heat treatment. (Steps 5 and 8 are optional.)

EXAMPLE II

A medium prepared as described in Example I is used to prepare a starter culture for making Mozzarella cheese. The inoculation and incubation may be carried out while maintaining a temperature in the medium of about 103±2° F. More specifically, the steps to be followed are:

1. Inoculate the medium with coccus and rod (*S. thermophilus* and *L. bulgaricus*) of thawed bacterial concentrate using 1 can (per 150 gal.) of starter medium.
2. Agitate the medium for 5 to 10 min. after adding the culture concentrate.
3. Shut off the agitator and incubate the medium until pH drops to 5.35±0.05. The medium should not coagulate.
4. When the pH drops to 5.35±0.05, start cooling the starter with agitation.
5. Cool the uncoagulated medium to 45° F. and hold until used for making Mozzarella cheese.

EXAMPLE III

A medium is prepared from nonfat dry milk and whey protein concentrate. The composition and preparation are set out below.

| Composition: | |
|---|---|
| Nonfat dry milk | 69 lbs. |
| Whey protein concentrate (28–33% protein) | 32 lbs. |
| Water | 738 lbs. |
| | 839 lbs. |

Preparation

Preparation is the same as for the medium described in Example I.

EXAMPLE IV

A medium is prepared from whey protein concentrate and casein. The composition and preparation are set out below.

| Composition: | |
|---|---|
| Whey protein concentrate (28–33% protein) | 150 lbs. |
| Trisodium phosphate | 15.25 oz. |
| Sodium hydroxide powder | 3 lbs. and 2 oz. |
| Casein | 55 lbs. |
| Silicone antifoamer | 8.92 oz. |
| Calcium chloride solution (35% CaCl$_2$) | 7 lbs. and 6.5 oz. |
| Water | 1032 lbs. |
| | 1250 lbs. |

Preparation

1. Clean, sanitize and fill the tank with two-thirds of the water (about 638 lbs.) as in Example I.
2. Warm the water to 110° F., and add the whey protein concentrate, trisodium phosphate, and sodium hydroxide with stirring until they are dissolved in the water.
3. Add the rest of the water, heat to 130° F., and then add the casein and antifoamer. Heat the water gradually to 150° F. with continual stirring. By that point, the casein should be in the sodium salt form and completely dissolved.
4. Add the calcium chloride solution.
5. Heat, cool, and sample the medium as described in steps 6 to 8 of Example I.

EXAMPLE V

A medium is prepared from whole milk, nonfat dry milk, and whey protein concentrate. Instead of whole milk, skimmilk or partially skimmed milk may be used. The composition and preparation are set out below.

| Composition: | |
|---|---|
| Whole milk | 1290 lbs. |
| Nonfat dry milk | 45 lbs. |
| Whey protein concentrate (28–33% protein) | 100 lbs. |
| | 1435 lbs. |

Preparation

1. Fill the cleaned and sanitized starter tank with whole milk.
2. Empty the dry ingredients into whole milk with the aid of a powder funnel. The temperature at this stage should be around 100° F.
3. Heat the medium to 170° F. and hold for 1 hour.
4. Cool the medium to 100° to 104° F.
5. Samples for determination of casein, whey protein, and total protein may be drawn before and after the heat treatment as in Example I.

EXAMPLE VI

A starter medium for making mozzarella cheese is prepared from partially delactosed whey, nonfat dry milk, and calcium caseinate. The composition of the medium and its preparation are set out below:

| Composition: | Puritein 25 | 67 lbs. |
|---|---|---|
| | Nonfat Dry Milk | 46 lbs. |
| | Calcium Caseinate | 45 lbs. |
| | Water | 1,160 lbs. |
| | | 1,318 lbs. |

Preparation

1. Clean and sanitize the starter tank.
2. Fill the tank with about ⅔ of water.
3. Heat the water to 110° F. and then add rest of the ingredients.
4. Agitate thoroughly until the ingredients are thoroughly mixed.
5. Add rest of the water to make it up to a total of 1,318 lbs. of liquid medium.
6. Heat the medium to 190° F. and hold for 1 hour. The medium should not show any sign of precipitation at this stage.
7. Cool the medium to 101° to 105° F.
8. Inoculate the medium with appropriate coccus and rod culture.
9. Incubate until pH drops to 5.35±0.05 and then start cooling the uncoagulated medium to 45° F. and hold until used for making mozzarella cheese. The medium is rennet coagulable.

Puritein 25 is a whey product of Purity Cheese Company, Mayville, Wis., which is prepared from sweet whey by removing part of the lactose and minerals and thereby increasing the protein content. A typical analysis is: protein 24–26%; lactose 50–53%; ash 13–15%; balance fat and moisture.

Instead of Puritein 25, Puritein 20 (Purity Cheese Company) can be used. This is a partially delactosed whey having as a typical analysis: protein 21–23%; lactose 49–51%; ash 19–21%; balance fat and moisture.

All of the foregoing examples represent desirable modes of practicing the present invention. The formula selected as the preferred mode for a particular commercial use will depend on the availability and price of the ingredients. Media prepared according to the examples may be used to prepare starter cultures for many kinds of cheese, such as Mozzarella, Swiss, Cheddar, etc. The media may also be used for preparing added cultures for preparing Mozzarella "pizza cheese" as described in U.S. Pat. No. 4,085,228. For example, a bulk starter culture prepared as described above in Example II for use in manufacturing Mozzarella cheese may be used in combination with an added culture using the medium of Example I and culturing *Streptococcus durans* therein, as described in the cited patent.

In practicing the present invention, it will be apparent to those skilled in the art that minor adjustments can be made where necessary to more completely achieve the objects of the invention. For example, if during the heating step the medium tends to coagulate, the casein content can be increased and/or the total solids concentration can be decreased. Further, on completion of the fermentation, if desired a calcium salt, such as calcium chloride, can be added to the starter culture before it is charged to the cheese vat, thereby further promoting the rennet-coagulability of the medium. In practicing the present invention in its preferred embodiments, however, such adjustments should rarely be necessary.

We claim:

1. The method of making cheese by using a starter culture medium which results in a curd-whey mixture substantially free from culture medium produced curd fines, said method comprising:

(a) forming an aqueous culture medium from protein-providing medium solids selected from the class consisting of (i) mixtures of whey solids and precipitated casein in the form of a water-dispersible casein salt or (ii) mixtures of whey solids and milk solids, or (iii) mixtures of whey solids, milk solids, and precipitated casein in the form of a water-dispersible casein salt, said whey solids consisting essentially of whey protein concentrate made from whey by ultrafiltration, said medium solids providing a weight ratio within the range from 0.4 to 5.0 parts of casein (casein basis) per part of total whey protein provided by said whey solids and said milk solids, the whey protein provided by said whey solids comprising at least 10% by weight of said medium solids;

(b) heating said culture medium at a pH of from 5.6 to 6.9 to a temperature of about 160° to about 195° F. for about 20 to about 90 minutes to cause the complexing of casein and whey protein without precipitating whey protein or coagulating the medium, said medium on completion of said heating being coagulable without containing added calcium or phosphate ions by addition of rennet at the rate of 3 ounces per 1000 pounds of medium with the medium at pH 6.2 and 92° F.;

(c) culturing harmless lactic acid-producing bacteria in the completed medium from step (b) to produce a bulk starter culture without coagulating said medium; and, thereafter, (d) using said bulk starter culture as a bacterial inoculant for milk in the manufacture of cheese by adding said bulk starter culture to cheese milk and coagulating the milk with rennet, whereby complexed whey protein and casein of the bulk starter culture coagulates with the milk protein to produce a curd-whey mixture which is substantially free of curd fines from the starter medium.

2. The method of claim 1 in which said medium solids provide a weight ratio of from 0.9 to 3.5 parts of casein (casein basis) per part of total whey protein.

3. The method of making cheese by using a starter culture medium which results in a curd-whey mixture substantially free from culture medium produced curd fines, said method comprising:

(a) forming an aqueous culture medium containing from 12 to 18 weight percent of protein-providing medium solids selected from the class consisting of (i) mixtures of whey solids and precipitated casein in the form of a water-dispersible salt, or (ii) mixtures of whey solids and milk solids, or (iii) mixtures of whey solids, milk solids, and precipitated casein in the form of a water-dispersible casein salt, said whey solids consisting essentially of whey protein concentrate made from whey by ultrafiltration, said medium solids providing a weight ratio within the range from 0.9 to 3.5 parts of casein (casein basis) per part of total whey protein provided by said whey solids and said milk solids, said whey solids comprising at least 30% of the total medium solids and providing at least 10% by weight of whey protein based on the medium solids;

(b) heating said culture medium at a pH of from 5.6 to 6.9 to a temperature of about 160° to about 195° F. for about 20 to about 90 minutes to cause the complexing of casein and whey protein without precipitating whey protein or coagulating the medium, said medium on completion of said heating being coagulable without containing added calcium or phosphate ions by addition of rennet at the rate of 3 ounces per 1000 pounds of medium with the medium at pH 6.2 and 92° F.;

(c) culturing harmless lactic acid-producing bacteria in the completed medium from step (b) to produce a bulk starter culture without coagulating said medium; and, thereafter, (d) using said bulk starter culture as a bacterial inoculant for milk in the manufacture of cheese by adding said bulk starter culture to cheese milk and coagulating the milk with rennet, whereby complexed whey protein and casein of the bulk starter culture coagulates with the milk protein to produce a curd-whey mixture which is substantially free of curd fines from the starter medium.

4. The method of claim 3 in which said medium solids comprise a mixture of whey solids and precipitated casein in water-dispersible salt form.

5. The method of claim 4 in which said precipitated casein is in the form of calcium or sodium caseinate.

6. The method of claim 3 in which said medium solids comprise a mixture of whey solids and milk solids.

7. The method of claim 3 in which said medium solids comprise a mixture of whey solids, milk solids, and precipitated casein in water-dispersible form.

8. The method of claim 7 in which said precipitated casein is in the form of calcium or sodium caseinate.

9. The method of making cheese by using a starter culture medium which results in a curd-whey mixture substantially free from culture medium produced curd fines, said method comprising:

(a) forming an aqueous culture medium containing from 6 to 21 weight percent of protein-providing medium solids selected from the class consisting of (i) mixtures of whey solids and calcium caseinate, or (ii) mixtures of whey solids and milk solids, or (iii) mixtures of whey solids, milk solids, and calcium caseinate, said whey solids consisting essentially of whey protein concentrate made from whey by ultrafiltration and containing from 28 to 50% protein, said media solids providing a weight ratio of from 0.9 to 3.5 parts of casein (casein basis) per part of total whey protein provided by said whey solids and said milk solids, the whey protein provided by said whey solids comprising at least 10% by weight of said medium solids and said whey solids comprising at least 30% by weight of the total medium solids;

(b) heating said culture medium at a pH of from 5.6 to 6.9 to a temperature of about 160° to about 195° F. for about 20 to about 90 minutes to cause the complexing of casein and whey protein without precipitating whey protein or coagulating the medium, said medium on completion of said heating being coagulable without containing added calcium or phosphate ions by addition of rennet at the rate of 3 ounces per 1000 pounds of medium with the medium at pH 6.2 and 92° F.;

(c) culturing harmless lactic acid-producing bacteria in the completed medium from step (b) to produce a bulk starter culture without coagulating said medium; and, thereafter, (d) using said bulk starter culture as a bacterial inoculant for milk in the manufacture of cheese by adding said bulk starter culture to cheese milk and coagulating the milk with rennet, whereby complexed whey protein and casein of the bulk starter culture coagulates with the milk protein to produce a curd-whey mixture which is substantially free of curd fines from the starter medium.

10. The method of claim 9 in which said medium contains from 12 to 18% of said medium solids.

11. The method of claim 9 or claim 10 in which said medium solids comprise a mixture of whey protein concentrate and calcium or sodium caseinate.

12. The method of claim 9 or claim 10 in which said medium solids comprise a mixture of whey protein concentrate, milk solids, and calcium or sodium caseinate, and at least 50% of the casein (casein basis) in said medium solids being provided by said caseinate.

13. The method of making cheese by using a starter culture medium which results in a curd-whey mixture substantially free from culture medium produced curd fines, said method comprising:
(a) forming an aqueous culture medium containing from 12 to 18 weight percent of protein-providing medium solids selected from the class consisting of (i) mixtures of whey solids and precipitated casein in the form of a water-dispersible salt, or (ii) mixtures of whey solids and milk solids, or (iii) mixtures of whey solids, milk solids, and precipitated casein in the form of a water-dispersible casein salt, said whey solids having been prepared from whey by increasing the amount of whey protein in relation to lactose and containing at least 20% by weight whey protein, said medium solids providing a weight ratio within the range from 0.9 to 3.5 parts of casein (casein basis) per part of total whey protein provided by said whey solids and said milk solids, said whey solids comprising at least 30% of the total medium solids and providing at least 10% by weight of whey protein based on the medium solids;
(b) heating said culture medium at a pH of from 5.6 to 6.9 to a temperature of about 160° to about 195° F. for about 20 to about 90 minutes to cause the complexing of casein and whey protein without precipitating whey protein or coagulating the medium, said medium on completion of said heating being coagulable without containing added calcium or phosphate ions by addition of rennet at the rate of 3 ounces per 1000 pounds of medium with the medium at pH 6.2 and 92° F.;
(c) culturing harmless lactic acid-producing bacteria in the completed medium from step (b) to produce a bulk starter culture without coagulating said medium; and, thereafter,
(d) using said bulk starter culture as a bacterial inoculant for milk in the manufacture of cheese by adding said bulk starter culture to cheese milk and coagulating the milk with rennet, whereby complexed whey protein and casein of the bulk starter culture coagulates with the milk protein to produce a curd-whey mixture which is substantially free of curd fines from the starter medium.

14. The method of claim 13 in which said medium solids comprise a mixture of whey solids and precipitated casein in water-dispersible salt form.

15. The method of claim 14 in which said precipitated casein is in the form of calcium or sodium caseinate.

16. The method of claim 13 in which said medium solids comprise a mixture of whey solids and milk solids.

17. The method of claim 13 in which said medium solids comprise a mixture of whey solids, milk solids, and precipitated casein in water-dispersible form.

18. The method of claim 17 in which said precipitated casein is in the form of calcium or sodium caseinate.

* * * * *